United States Patent [19]

Motta

[11] 4,330,477

[45] May 18, 1982

[54] PROCESS FOR OBTAINING HIGH-PURITY TRICYCLOHEXYL TIN HYDROXIDE ON A HIGH-YIELD BASIS

[75] Inventor: Raimondo Motta, Milan, Italy

[73] Assignee: Oxon Italia S.p.A., Pero, Italy

[21] Appl. No.: 151,594

[22] Filed: May 20, 1980

[30] Foreign Application Priority Data

Jun. 27, 1979 [IT] Italy ................................ 23893 A/79

[51] Int. Cl.³ ................................................. C07F 7/22
[52] U.S. Cl. .................................................. 260/429.7
[58] Field of Search ....................................... 260/429.7

[56] References Cited

U.S. PATENT DOCUMENTS

| | | | |
|---|---|---|---|
| 3,010,979 | 11/1961 | Ramsden | 260/429.7 |
| 3,067,226 | 12/1962 | Ramsden | 260/429.7 |
| 3,355,468 | 11/1967 | Hirshman et al. | 260/429.7 |
| 3,355,470 | 11/1967 | Natoli | 260/429.7 |
| 3,402,189 | 9/1968 | Natoli | 260/429.7 |
| 3,607,891 | 9/1971 | Kushlefsky et al. | 260/429.7 |
| 4,174,346 | 11/1979 | Collins et al. | 260/429.7 |

*Primary Examiner*—Helen M. S. Sneed
*Attorney, Agent, or Firm*—Young & Thompson

[57] ABSTRACT

A process for producing tricyclohexyl tin derivatives, consists of a first phase in which Grignard reagent and tin tetrahalogenide are caused to react by feeding them into a reaction vessel in a molar ratio of 3:1, and a second phase in which after hydrolysis and anhydridization of the condensation mass, further Grignard reagent is added in an amount such as to maintain the total molar ratio, between the Grignard reagent and the tin tetrahalogenide, between 3.5:1 and 3.9:1.

4 Claims, 3 Drawing Figures

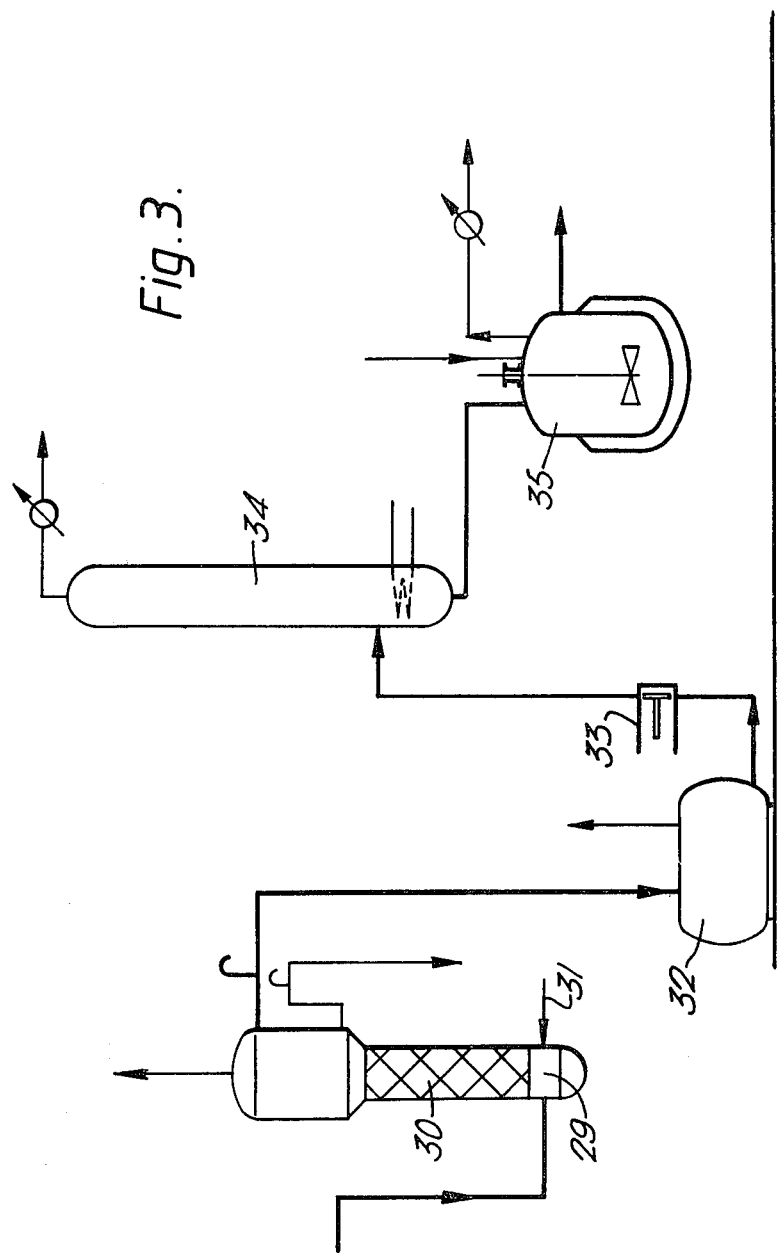

PROCESS FOR OBTAINING HIGH-PURITY TRICYCLOHEXYL TIN HYDROXIDE ON A HIGH-YIELD BASIS

BACKGROUND OF THE INVENTION

The present invention relates to important improvements in the production of tricyclohexyl tin hydroxide from cyclohexyl magnesium halogenide and from tin tetrahalogenide. More particularly, the invention concerns a method which enables a very high-quality product to be obtained in almost the theoretically possible quantities, without requiring any purification process either on the intermediate products or on the finished products, and without isolating any intermediate phase.

The process in accordance with the invention may be carried out either discontinuously or continuously.

The continuous process offers particular advantages in industrial practice, the Applicants having carried out trials in their own works over a fairly lengthy period with excellent results.

It is known from the literature on the subject that when Grignard reagent is caused to react with tin tetrahalogenide, so as to obtain tricyclohexyl tin halogenide the following reactions take place simultaneously:

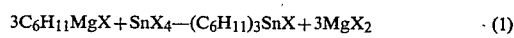  (1)

(principal reaction)

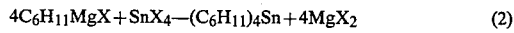  (2)

(secondary reaction)

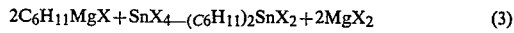  (3)

(secondary reaction)

wherein $X = Cl, Br$.

It is also known that the importance of the secondary reactions (2) and (3) is associated with the type of technique used in the production process, and that the tetracyclohexyl tin and the dicyclohexyl tin dehalogenide that form during reactions (2) and (3) must be eliminated (if present) from the principal tricyclohexyl tin halogenide product so as not adversely to affect the quality of the final tricyclohexyl tin hydroxide product that it is required to obtain.

In fact, when the products of the reactions (1), (2) and (3) are subjected to the subsequent reaction with caustic alkali, so as to obtain the final required product, the tetracyclohexyl tin remains unchanged, the dicyclohexyl tin dihalogenide is converted into dicyclohexyl tin oxide in the reaction:

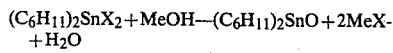

wherein $X = Cl, Br$ $Me = Na, K$ etc. and the tricyclohexyl tin halogenide is converted into the required tricyclohexyl tin hydroxide in the reaction:

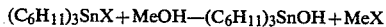

wherein $X = Cl, Br$ $Me = Na, K$ etc.

Italian patent Nos. 967587 and 1002391 which describe techniques which are improved in respect of the previously known processes, have already provided the teaching which enables the formation of tetracyclohexyl tin to be avoided. However, it has not yet been possible to avoid the presence of dicyclohexyl tin dihalogenide in the final product resulting from the reaction between tin halogenide and Grignard reagent, by any technique yet described in the literature. Consequently, it has always been necessary hitherto to carry out purification in a phase following condensation involving the Grignard reagent and tin tetrahalogenide. Such purification consists either in the alcoholic crystallization of the tricyclohexyl tin halogenide or in the elimination by filtration of the dicyclohexyl tin oxide which forms during the reaction with caustic alkali.

SUMMARY OF THE INVENTION

The need for purification of the product in question is now eliminated by means of the present invention, which provides a procedure in which dicyclohexyl tin dihalogenide is converted into tricyclohexyl tin halogenide by reacting it, under suitable conditions, with Grignard reagent in accordance with the following reaction:

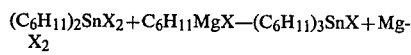

wherein $X = Cl, Br$
in the presence of previously formed tricyclohexyl tin halogenide, without the formation of tetracyclohexyl tin.

More particularly, the present invention relates to a process whereby the Grignard reagent is added in two lots, namely 80–90% in a first condensation and 20–10% in a second condensation which follows the completion of the first condensation.

As will be shown in further detail hereinafter, by adding the Grignard reagent in two separate lots, it becomes possible, in a surprising and advantageous manner, to overcome the condition—hitherto binding for any other technique in use—whereby, to carry out successful synthesis, the molar ratio between the Grignard reagent and tin tetrahalogenide should in no case exceed the value 3:1, if wishing to avoid the forming of substantial quantities of tetracyclohexyl tin.

In the present invention such ratio can be exceeded (varying from 3.5:1 to 3.9:1) without the formation of tetracyclohexyl tin, with the important consequence that the reaction can be completed by eliminating the dicyclohexyl tin dihalogenide which it has not been possible to cause to react in the known techniques. The success of this operation has resulted in a further very important advantage, namely the use of an entirely continuous process of synthesis and of production equipment for carrying out the process.

To summarize, the present invention relates to a procedure for the production of tricyclohexyl tin derivatives, characterized essentially in that, in a first phase, Grignard reagent and tin tetrahalogenide are caused to react by feeding them into a reaction vessel in a molar ratio of 3:1 and in that, in a second phase, after hydrolysis and anhydridization of the condensation mass, further Grignard reagent is added in an amount such as to obtain a total molar ratio between the Grignard reagent and the tin tetrahalogenide of between 3.5:1 and 3.9:1.

The above-mentioned procedure can be carried out either as a continuous process or as a discontinuous process.

BRIEF DESCRIPTION OF THE DRAWINGS

The heretoattached drawings, which are constituted of three sequential sheets of a flow diagram schematically illustrate an apparatus for continuously carrying out the process according to the present invention.

DESCRIPTION OF THE PREFERRED EMBODIMENTS

Figure 1:
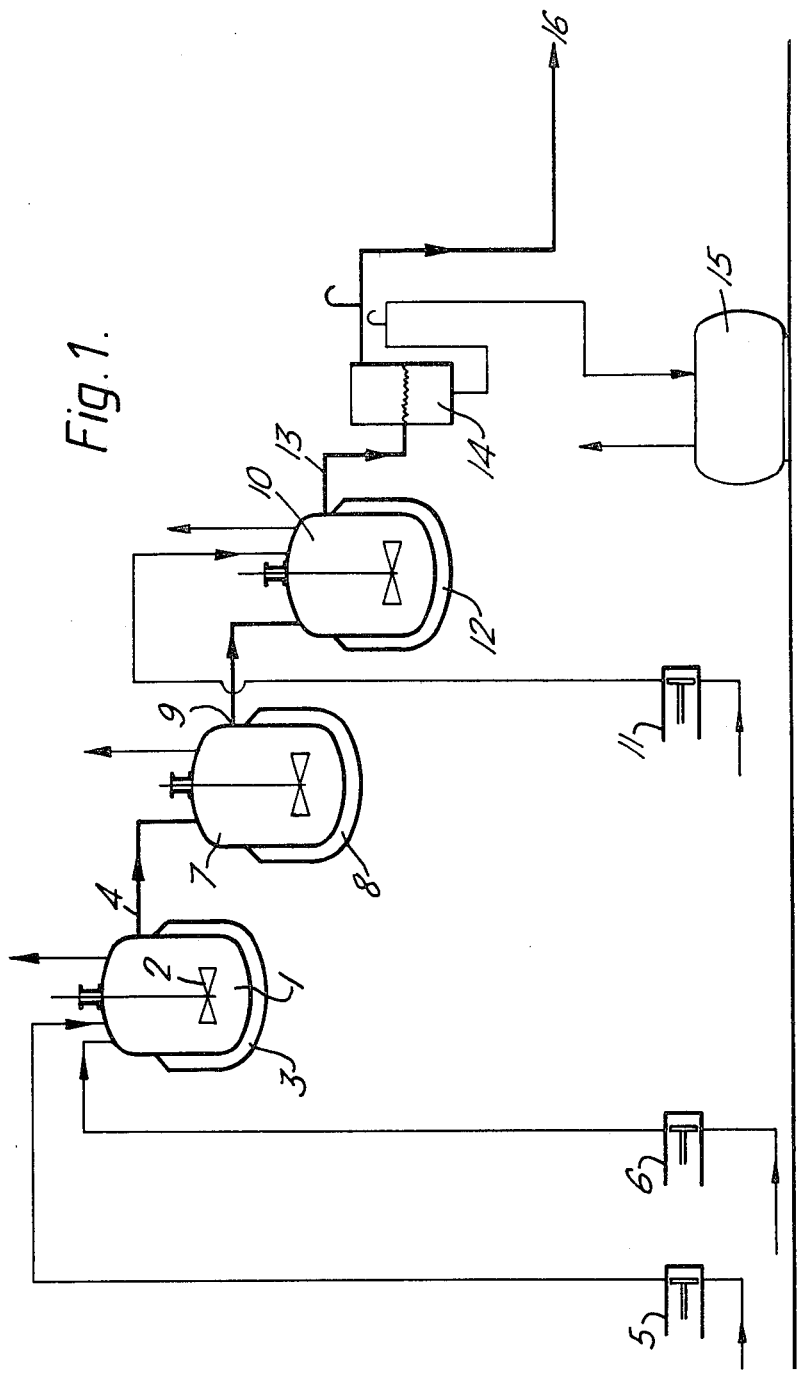
Figure 2:
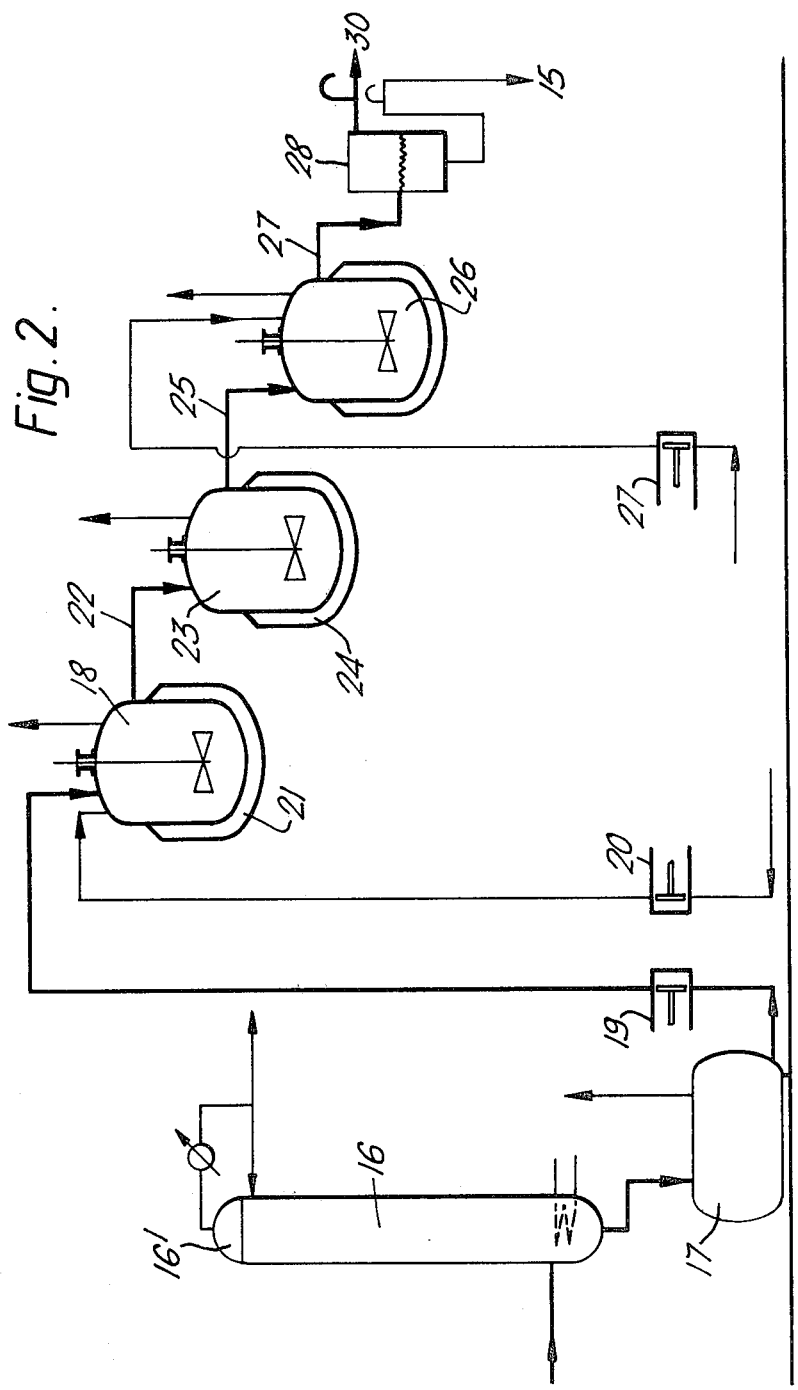

In the case where a continuous process is used, the invention provides that this comprises the following operations carried out in succession:

preparation of the Grignard reagent (in accordance with the procedure described in Italian patent application No. 24100 A/75);

condensation of the tin tetrahalogenide and the Grignard reagent, which condensation is carried out by adding the two reagents simultaneously in a reaction vessel and in a molar ratio of 3:1, Grignard to tin, throughout the reaction (and therefore under the conditions described in Italian patent No. 967587);

hydrolysis of the condensation mass obtained, followed by separation of the organic phase;

anhydridization and concentration of the organic phase containing the tricyclohexyl tin halogenide and the dicyclohexyl tin dihalogenide;

condensation of the concentrated mass by means of a further amount of Grignard reagent;

hydrolysis of the condensation mass followed by separation of the organic phase;

reaction of the tricyclohexyl tin halogenide, contained in this organic phase, with caustic alkali;

distillation, with steam, of the solvents; and filtration of the finished product.

If however, the process is carried out on a discontinuous basis, the invention is achieved by separately preparing the Grignard reagent complexed with tetrahydrofurane and the complex of tin tetrahalogenide also with tetrahydrofurane (using, respectively, the procedures described in Italian patent application No. 24100 A/75 and Italian Pat. No. 1002391), by then adding progressively the Grignard reagent complex to the tin tetrahalogenide complex to give a Grignard to tin molar ratio of 3:1, hydrolysing and anhydridizing the condensation mass obtained, and finally adding a further amount of Grignard reagent in such quantity that the total molar ratio of the latter to the tin tetrahalogenide is between 3.5:1 and 3.9 to 1, so as to obtain tricyclohexyl tin oxide after hydrolysis, reaction with caustic alkali, distillation and filtration.

The continuous process is particularly interesting and advantageous for the reasons detailed below. It is therefore important to describe in greater detail the operational features that characterize this process.

When this method, in accordance with the present invention, is used on a practical basis, the Grignard reagent (obtained from the continuous production plant described in Italian patent application No. 24100 A/75) is first of all reacted with the tin tetrahalogenide in an inert solvent, preferably toluol, these materials being fed simultaneously into a reaction vessel in a stoichiometric molar ratio of 3:1 by means of metering pumps, the reaction temperature being kept at 35°-55° C. and preferably 42°-46° C., while vigorously stirring the mixture. The compound issues from the overflow of the reaction vessel and passes into a second finishing, reaction vessel which is kept at a temperature of 60°-75° C., and preferably 65°-68° C. The compound discharging from the overflow of this reaction vessel passes into a further reaction vessel where it is hydrolyzed, while at the same time an acid solution, preferably a 5% hydrochloric acid solution, is added by means of a metering pump.

The compound issuing from the overflow is separated in a liquid-liquid separator, and the organic phase is fed into a distillation column, is anhydrized and concentrated to approximately 50% of its initial volume.

The concentrated compound issuing from the distillation column is fed into a reaction vessel together with Grignard reagent by means of metering pumps, in such a way that the molar ratio of the Grignard reagent and the SnX$_4$ ranges from 3.5-3.9:1, and is preferably 3.7:1.

The temperature in the reaction vessel is maintained at 35°-50° C., and preferably at 40°-45° C.

The compound issuing from the overflow of the reaction vessel is passed into a further finishing reaction vessel which is maintained at a temperature of 40°-60° C. and preferably at 45°-50° C.

The compound issuing from the overflow of this reaction vessel passes into yet another reaction vessel where it is hydrolyzed, while at the same time an acid solution, preferably a 15% hydrochloric acid solution, is added by means of a metering pump.

The compound issuing from the overflow is separated in a liquid-liquid separator, and the organic phase is passed through a porous diaphragm at the bottom of a column filled with Raschig rings and containing an aqueous caustic alkali, preferably 15% caustic soda. At the same time, a metering pump supplies the bottom of the column with aqueous caustic alkali, preferably 15% NaOH, so that the molar ratio

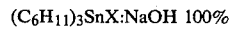
$(C_6H_{11})_3SnX:NaOH\ 100\%$ is 1:1.5-2.5, and preferably 1:2. The temperature in the column is kept at 60°-75° C., and preferably 68°-70° C.

The organic phase, separated from the aqueous phase, that issues at the top of the column, is distilled so as to eliminate the solvents, and the tricyclohexyl tin hydroxide is separated by filtration and then dried.

A product of 96-98% purity is obtained, with a yield of 95-96% calculated on the basis of the Sn tetrahalogenide.

This continuous process results in considerable advantages, the main ones of which are:

a very high production potential; for example with equipment of a volume of between 10 and 20 liters, 150-200 kg of finished product can be produced each day;

almost complete elimination of the processing dangers connected with the production and use of Grignard reagent, in view of the small quantities of products present in the working line;

a very high yield and the total absence of side-products derived from tin and difficult to dispose of or destroy, thus resulting in the well-known ecological problems;

a high and constant quality in the finished product without the need for more or less complicated purification operations;

stirring can be carried out easily and efficiently, and the heat of reaction can be readily dissipated in view of the small dimensions of the equipment.

The following examples are provided for the purpose of illustrating the invention and of making it more comprehensible. However the invention is in no way limited to these examples.

EXAMPLE 1

This first example relates to a process of the continuous type in accordance with the invention, and the description thereof refers to the attached drawings consisting, as signified above, of three sequential sheets which illustrate the equipment for carrying out said process.

A reaction vessel 1, equipped with stirring means 2, a thermometer, a gravity cooling system, an outer cooling jacket 3 and a lateral overflow discharge line 4, and having a useful capacity of 15 liters to the overflow while stirring, is charged with 3 liters toluol; and 1 liter tetrahydrofurane.

simply for the purpose of starting the equipment, so as to facilitate stirring and not to start with an empty reaction vessel. Subsequently or in any case when the equipment is started, the following are simultaneously added by means of metering pumps 5 and 6:

23.8 liters/hour of a solution of cyclohexyl magnesium chloride in tetrahydrofurane, emanating from an apparatus for continuously producing Grignard reagent, of the type described in Italian patent application No. 24100 A/75, this material corresponding to 7.63 kg/hour at 100% = 0.053 kmol/hour: and 35 liters/hour of a toluenic solution of tin tetrachloride corresponding to 4.64 kg/hour of $SnCl_4$ 100% = 0.0178 kmol/hour.

Therefore the reagents are introduced in such a way that they react in the 3:1 tin tetrachloride/Grignard reagent molar ratio, in accordance with the teachings of Italian Pat. No. 967587 in the name of the present assignee.

Water is caused to circulate in the jacket 3 of the reaction vessel 1 at a temperature such that the vessel is maintained at a temperature of between 42° and 46° C.

Stirring should be carried out efficiently so as to facilitate heat-exchange and to avoid local overheating.

When the reaction vessel is full, the reaction composition runs out through the lateral overflow 4 and falls into a second reaction vessel 7 similar to the vessel 1. The reaction is completed in this vessel 7 and a temperature of between 65° and 68° C. is reached. This temperature is kept constant in the reaction vessel by circulating hot water in the jacket 8 of the vessel 7.

The compound that escapes through the lateral overflow 9 of the reaction vessel 7 falls into a hydrolyzing vessel 10 having the same dimensions as the previous ones, but made of acid-resisting material. Simultaneously with the composition issuing from the reaction vessel 7, 14 liters of 5% hydrochloric acid per hour are fed to the reaction vessel 10 by means of a metering pump 11.

In the vessel 10, the temperature is maintained at 35°-40° C. by cooling with water in the jacket 12 of this vessel.

The hydrolysis composition which is formed in the reaction vessel 10 and is made up of an organic phase containing tricyclohexyl tin chloride and dicyclohexyl tin dichloride and of an aqueous acid phase, containing magnesium chloride, passes through the lateral overflow 13 of the vessel 10 and into the liquid-liquid separator 14 in which separation of the two phases takes place.

The acid phase is eliminated by passing it into a tank 15, whereas the organic phase is fed to a distillation column 16 to be concentrated and anhydrized.

The distilled solvents emerge from the top 16' of the column 16 and are passed on for collection, whereas from the bottom of the column a concentrated solution emerges at a rate of 30 liters per hour and is collected in a tank 17.

Into a reaction vessel 18 (similar to the vessel 1 and located downstream of the column 16), by means of metering pumps 19 and 20 respectively, are simultaneously fed, 30 liters/hour of the concentrated solution obtained in the tank 17; and 5.6 liters/hour of cyclohexyl magnesium chloride in a solution of tetrahydrofurane, corresponding to 1.792 kg/hour at 100% = 0.0125 kmol/hour.

The temperature in the reaction vessel is maintained at 40°-45° C. by the circulation of water in the jacket 21 of the reaction vessel 18.

The composition issues through a side overflow 22 of the reaction vessel 18 and falls into a finishing reaction vessel 23 similar to the vessel 1. In the reaction vessel 23, the temperature is maintained at 45°-50° C. by the circulation of hot water in the jacket 24 of this vessel 23.

From a lateral overflow 25 of the reaction vessel 23, the reaction composition falls into a further reaction vessel 26, which is similar to the vessel 12 and into which are simultaneously fed, through a metering pump 27:

3.5 liters/hour of 15% hydrochloric acid.

The hydrolyzed composition resulting therefrom consists of an organic phase containing tricyclohexyl tin chloride, and of an acid aqeuous phase containing magnesium chloride, and said composition issues from a side overflow 27 of the reaction vessel 26 and passes to the liquid-liquid separator 28 wherein the two phases are separated.

The acid phase is eliminated by passing it to the tank 15, whereas the organic phase is passed through a porous diaphragm 29 into the bottom of a column 30, having a diameter of approximately 10 cm and a height of approximately 150 cm, filled with Raschig rings and containing 15% caustic soda up to the top outlet.

8.15 liters/hour of 15% NaOH are further added through a feed 31 into the bottom of the column 30, simultaneously with the organic solution.

The temperature in the column is maintained at 70° C. by means of hot water circulating in the jacket. Also the added reagents are preheated.

The top of the column 30 is designed to act as a liquid-liquid separator so that the organic tricyclohexyl tin hydroxide solution and the alkaline aqueous phase come out from the column simultaneously, but separately. The alkaline aqueous phase is then eliminated.

The organic phase, collected in the tank 32, is passed by means of a metering pump 33 to a distillation apparatus consisting of a preconcentration column 34 and a distillator 35, where the residual solvents are eliminated by distillation with steam.

The tricyclohexyl tin hydroxide is then filtered and dried.

6.52 Kg/hour of tricyclohexyl tin hydroxide of 96.8% titre are obtained.

The yield calculated on the basis of the tin tetrachloride is 95% of theory.

EXAMPLE 2

This second example relates to a discontinuous process in accordance with the invention.

400 ml of anhydrous toluol, and 80 g of tin tetrachloride=0.307 mol are fed into a reaction vessel provided with stirring means, a thermometer and gravity cooling means.

60 ml of tetrahydrofurane=0.74 mol are fed into the solution obtained, at a temperature of between 0° and 5° C.

The complex $SnX_4.2R'_2O$ (see Italian Pat. No. 1002391 in this connection) is obtained in the form of a white crystalline precipitate.

While maintaining the temperature at 38°-42° C., 411 g of cyclohexyl magnesium chloride in tetrahydrofurane =131.5 g at 100%=0.921 mol (prepared as described in Italian patent application No. 24100 A/75) are added to this composition over a period of approximately 30 minutes.

The mixture is heated to 70° C. and is maintained at that temperature for 30 minutes.

After cooling, 200 ml of 5% HCl are added.

The organic phase is separated from the aqueous phase. The organic phase is concentrated to approximately half its initial volume, by distillation.

71 g of cyclohexyl magnesium chloride solution in tetrahydrofurane=22.7 g at 100%=0.159 mol are added to the concentrated solution over a period of about 30 minutes and at a temperature of between 40° and 45° C.

The mixture is held at 40°-45° C. for 30 minutes.

50 ml of 15% HCl are then added.

The organic phase is then separated from the aqueous phase.

82 g of 15% NaOH=0.614 mol are added to the organic phase.

The mixture is heated to 70° C. and is held at this temperature for 1 hour.

The organic phase is separated from the aqueous phase.

The solvents are distilled with steam.

The white crystalline product obtained is filtered, washed with water and dried.

113 g of tricyclohexyl tin hydroxide are obtained. Yield: 95.6%.

Titre of the product: 96%.

I claim:

1. A process for producing tricyclohexyl tin hydroxide, comprising reacting 3 mols of cyclohexyl magnesium halide with 1 mol of tin tetrahalide, hydrolyzing the reaction product, separating water from the reaction product, and thereafter adding further cyclohexyl magnesium halide to the reaction product until the mol ratio between the cyclohexyl magnesium halide and the tin tetrahalide is between 3.5:1 and 3.9:1.

2. A process as claimed in claim 1, and thereafter filtering the reaction product.

3. A process as claimed in claim 1, which is continuous.

4. A process as claimed in claim 1, which is a batch process, in which the cyclohexyl magnesium halide and tin tetrahalide are complexed with tetrahydrofurane.

* * * * *